(12) United States Patent
Brain (10) Patent No.: US 7,896,007 B2
(45) Date of Patent: *Mar. 1, 2011

(54) INTUBATING LARYNGEAL MASK AIRWAY DEVICE WITH FIBER OPTIC ASSEMBLY

(75) Inventor: Archibald I. J. Brain, Les Bons Villers (BE)

(73) Assignee: Indian Ocean Medical Inc., Mahe (SC)

( * ) Notice: Subject to any disclaimer, the term of this patent is extended or adjusted under 35 U.S.C. 154(b) by 965 days.

This patent is subject to a terminal disclaimer.

(21) Appl. No.: 11/588,831

(22) Filed: Oct. 27, 2006

(65) Prior Publication Data
US 2007/0119460 A1 May 31, 2007

Related U.S. Application Data

(63) Continuation of application No. 10/659,455, filed on Sep. 10, 2003, now Pat. No. 7,128,071.

(51) Int. Cl.
*A61M 16/00* (2006.01)
*A61M 29/00* (2006.01)

(52) U.S. Cl. .......... 128/207.15; 128/200.26; 128/207.14; 128/207.16; 604/96.01

(58) Field of Classification Search ............. 128/207.14, 128/207.15, 207.16, 200.26; 604/96.01
See application file for complete search history.

(56) References Cited

U.S. PATENT DOCUMENTS

| | | |
|---|---|---|
| 2,839,788 A | 6/1958 | Dembiak |
| 2,862,498 A | 12/1958 | Weekes |
| 3,554,673 A | 1/1971 | Schwartz et al. |
| 3,931,822 A | 1/1976 | Marici |
| 4,104,357 A | 8/1978 | Blair |
| 4,231,365 A | 11/1980 | Scarberry |
| 4,509,514 A | 4/1985 | Brain et al. |
| 4,553,540 A | 11/1985 | Straith |
| 4,700,700 A | 10/1987 | Eliachar |
| 4,793,327 A | 12/1988 | Frankel |
| 4,846,153 A | 7/1989 | Berci |
| 4,850,371 A | 7/1989 | Broadhurst et al. |
| 4,872,483 A | 10/1989 | Shah |

(Continued)

FOREIGN PATENT DOCUMENTS
CA 2067782 6/1999

(Continued)

OTHER PUBLICATIONS

Abdelatti, "A cuff pressure controller for tracheal tubes and laryngeal mask airway," Anaesthesia 1999, 54 pp. 981-986.

(Continued)

*Primary Examiner* — Patricia M Bianco
*Assistant Examiner* — Nihir Patel
(74) *Attorney, Agent, or Firm* — Wilmer Cutler Pickering Hale and Dorr LLP (57) ABSTRACT

The disclosed laryngeal mask airway device includes a rigid airway tube, a mask portion, and a viewing system. The mask portion is inflatable and can be inserted, when deflated, through a patient's mouth to a location near the patient's glottic opening. The mask portion also includes an epiglottis elevator bar and a distal end of the bar defines an aperture. The viewing system has a proximal end located outside the patient. The viewing system also has a distal end positioned so that light rays can pass from a portion of the patient's anatomy, through the aperture in the elevator bar, and into the distal end of the viewing system.

8 Claims, 5 Drawing Sheets

U.S. PATENT DOCUMENTS

| | | | |
|---|---|---|---|
| 4,953,547 | A | 9/1990 | Poole, Jr. |
| 4,995,388 | A | 2/1991 | Brain et al. |
| 5,038,766 | A | 8/1991 | Parker |
| 5,174,283 | A | 12/1992 | Parker |
| 5,193,544 | A | 3/1993 | Jaffe |
| 5,235,973 | A | 8/1993 | Levinson |
| 5,241,956 | A | 9/1993 | Brain et al. |
| 5,249,571 | A | 10/1993 | Brain et al. |
| 5,277,178 | A | 1/1994 | Dingley et al. |
| 5,282,464 | A | 2/1994 | Brain et al. |
| 5,285,778 | A | 2/1994 | Mackin |
| 5,297,547 | A | 3/1994 | Brain et al. |
| 5,303,697 | A | 4/1994 | Brain et al. |
| 5,339,805 | A | 8/1994 | Parker |
| 5,339,808 | A | 8/1994 | Don Michael |
| 5,355,879 | A | 10/1994 | Brain et al. |
| 5,391,248 | A | 2/1995 | Brain et al. |
| 5,477,851 | A | 12/1995 | Callaghan et al. |
| 5,487,383 | A | 1/1996 | Levinson |
| 5,529,582 | A | 6/1996 | Fukuhara et al. |
| 5,569,219 | A | 10/1996 | Hakki et al. |
| 5,582,167 | A | 12/1996 | Joseph |
| 5,584,290 | A | 12/1996 | Brain et al. |
| 5,599,301 | A | 2/1997 | Jacobs et al. |
| 5,623,921 | A | 4/1997 | Kinsinger et al. |
| 5,632,271 | A | 5/1997 | Brain et al. |
| RE35,531 | E | 6/1997 | Callaghan et al. |
| 5,642,730 | A | 7/1997 | Baran et al. |
| 5,653,229 | A | 8/1997 | Greenberg |
| 5,655,528 | A | 8/1997 | Pagan et al. |
| 5,682,880 | A | 11/1997 | Brain et al. |
| 5,694,929 | A | 12/1997 | Christopher |
| 5,711,293 | A | 1/1998 | Brain et al. |
| 5,738,094 | A | 4/1998 | Hoftman |
| 5,743,254 | A | 4/1998 | Parker |
| 5,743,258 | A | 4/1998 | Sato et al. |
| 5,746,202 | A | 5/1998 | Pagan et al. |
| 5,771,889 | A | 6/1998 | Pagan et al. |
| 5,791,341 | A | 8/1998 | Bullard |
| 5,850,832 | A | 12/1998 | Chu |
| 5,865,176 | A | 2/1999 | O'Neil |
| 5,878,745 | A | 3/1999 | Brain |
| 5,881,726 | A | 3/1999 | Neame |
| 5,896,858 | A | 4/1999 | Brain |
| 5,915,383 | A | 6/1999 | Pagan |
| 5,937,860 | A | 8/1999 | Cook |
| 5,979,445 | A | 11/1999 | Neame et al. |
| 5,983,897 | A | 11/1999 | Pagan |
| 5,988,167 | A | 11/1999 | Kamen |
| 5,996,582 | A | 12/1999 | Turnbull |
| 6,003,510 | A | 12/1999 | Anunta |
| 6,003,514 | A | 12/1999 | Pagan |
| 6,012,452 | A | 1/2000 | Pagan |
| 6,021,779 | A | 2/2000 | Pagan |
| 6,050,264 | A | 4/2000 | Greenfield |
| 6,070,581 | A | 6/2000 | Augustine et al. |
| 6,079,409 | A | 6/2000 | Brain et al. |
| D429,811 | S | 8/2000 | Bermudez et al. |
| 6,095,144 | A | 8/2000 | Pagan |
| 6,116,243 | A | 9/2000 | Pagan |
| 6,119,695 | A | 9/2000 | Augustine et al. |
| 6,240,922 | B1 | 6/2001 | Pagan |
| 6,390,093 | B1 | 5/2002 | Mongeon |
| 6,427,686 | B2 | 8/2002 | Augustine et al. |
| 6,439,232 | B1 | 8/2002 | Brain |
| 6,626,169 | B2 | 9/2003 | Gaitini et al. |
| 6,705,318 | B1 | 3/2004 | Brain |
| 7,128,071 | B2 * | 10/2006 | Brain ............ 128/207.15 |
| 2003/0131845 | A1 | 7/2003 | Lin |

FOREIGN PATENT DOCUMENTS

| | | |
|---|---|---|
| CA | 2012750 | 8/1999 |
| EP | 0389272 | 9/1990 |
| EP | 0402872 | 12/1990 |
| EP | 0294200 | 4/1992 |
| EP | 0580385 | 5/1996 |
| EP | 0712638 | 5/1996 |
| EP | 0732116 A2 | 9/1996 |
| EP | 0796631 | 9/1997 |
| EP | 0845276 | 6/1998 |
| EP | 0865798 | 9/1998 |
| EP | 0922465 | 6/1999 |
| EP | 1125595 | 8/2001 |
| GB | 2111394 | 12/1982 |
| GB | 2205499 | 6/1987 |
| GB | 2317342 | 8/1997 |
| GB | 2317830 | 9/1997 |
| GB | 2318735 | 10/1997 |
| GB | 2319478 | 10/1997 |
| GB | 2321854 | 1/1998 |
| GB | 2323289 | 2/1998 |
| GB | 2323290 | 3/1998 |
| GB | 2323291 | 3/1998 |
| GB | 2323292 | 3/1998 |
| GB | 2359996 | 9/2001 |
| JP | 10118182 | 5/1998 |
| JP | 10216233 | 8/1998 |
| JP | 10263085 A | 10/1998 |
| JP | 10263086 | 10/1998 |
| JP | 10277156 | 10/1998 |
| JP | 10314308 | 12/1998 |
| JP | 10323391 | 12/1998 |
| JP | 10328303 | 12/1998 |
| JP | 11128349 | 5/1999 |
| JP | 11192304 | 7/1999 |
| JP | 11206885 | 8/1999 |
| WO | WO-91/03207 | 3/1991 |
| WO | WO-91/07201 | 5/1991 |
| WO | WO-91/12845 | 9/1991 |
| WO | WO-92/13587 | 8/1992 |
| WO | WO-95/33506 | 12/1995 |
| WO | WO-97/12640 | 4/1997 |
| WO | WO-97/12641 | 4/1997 |
| WO | WO-98/16273 | 4/1998 |
| WO | WO-99/06093 | 2/1999 |
| WO | WO-00/09189 | 2/2000 |
| WO | WO-00/22985 | 4/2000 |
| WO | WO-0023135 | 4/2000 |
| WO | WO-00/61212 | 10/2000 |

OTHER PUBLICATIONS

Benumof J.L. "Management of the difficult airway with special emphasis on awake tracheal intubation," Anesthesiol, 1991, 75;6:1087.

Benumof, "Laryngeal Mask Airway and the ASA Difficult Airway Algorithm," Anesthesiology 1996;v84 No. 3:686-99.

Bernhard, et al., "Adjustment of Intracuff Pressure to Prevent Aspiration," Anesthesiology v. 50 No. 4:363-366, 1979.

Bernhard, et al., "Physical Chracteristics of an Rates of Nitrous Oxide Diffusion into Tracheal Tube Cuffs," Anesthesiology 48:413-417 1978.

Brain, "The Laryngeal Mask—A New Concept in Airway Management," Br. J. Anesth. (1983), vol. 55, pp. 801-805.

Brain, "The laryngeal mask airway—a possible new solution to airway problems in the emergency situation," Archives of Emergency Medicine, 1984, 1, 229-232.

Brain, "The laryngeal mask airway," Anaesthesia, 1985, vol. 40, pp. 356-361.

Brain, "Three cases of dfficult intubation overcome by the laryngeal mask airway," Anaesthesia, 1985, vol. 40, pp. 353-355.

Brain, et al., "A new laryngeal mask prototype," Anaesthesia, 1995, vol. 50, pp. 42-48.

Brimacombe, "The split laryngeal mask airway," p. 639.

Broderick, "The laryngeal mask airway," (1989) Anaesthesia, vol. 44, pp. 238-241.

Burgard, et al., "the Effect of Laryngeal Mask Cuff Pressure on Postoperative Sore Throat Incidence," J. of Clinical Anesthesia 8:198-201, 1996.

Caplan R.A., Posner K.L., Wend R.J., Cheney F.W., "Adverse respiratory events in anesthesia: a closed claims anaylsis", Anesthesiol, 1990, 72:828-833.

Craven, "Prevention of Hospital-Acquired Pneumonia: Measuring Effect in Ounces, Pounds, and Tons," Annals of Internal Medicine, vol. 122, No. 3, pp. 229-231 Feb. 1, 1995.

Cuff-Pressure-Control CDR 2000, LogoMed.

Davies, et al., "Laryngeal mask airway and tracheal tube insertion by unskilled personnel," The Lancet, vol. 336, pp. 977-979.

DeMello, et al., "The use of the laryngeal mask airway in primary anaesthesia," Anaesth. Corresp. (1990) 45,9:793.

Doyle et al., "Intraoperative Awareness: A Continuing Clinical Problem." http://doyle.ibme.utoronto.ca/anesthesia/aware.html.

Engbers, "Practical use of 'Diprifusor' systems", Anaesthesia 1998, 53, Suppl. 1, pp. 28-34.

Eriksson, et al., "Functional Assessment of the Pharynx at Rest and during Swallowing in Partially Paralyzed Humans," Anesthesiology vol. 87, No. 5, Nov. 1997, pp. 1035-1042.

Glen, "The development of 'Diprifusor': a TCI system for propofol," Anaesthesia 1998, 53, Suppl. 1, pp. 13-21.

Gray et al., "Development of the technology for 'Diprifusor' TCI systems," Anaesthesia 1998, 53, Suppl. 1, pp. 22-27.

Heath, "Endotracheal Intubation through the Laryngeal Mask—helpful when laryngoscopy is difficult or dangerous," European Journal of Anaesthesiology 1991, Suppl. 4, 41-45.

Hickey, et al., "Cardiovascular response to insertion of Brain's laryngeal mark," Anasth. Corresp. 1990, vol. 45 pp. 629-633.

Inomata, et al., "Transient Bilateral Vocal Cord Paralysis after insertion of a Laryngeal Mask Airway," Anesthesiology, 82:787-788, 1995.

Jacobson et al., A Study of Intracuff Pressure Measurements, Trends and Behaviours in Patients During Prolonged Periods of Tracheal Intubation, Br. J. Anaesth,1981, 53, 97.

Kambix, et al., "Intubation Lesions of the Larynx," Br. J. Anasth, 1978, 50, 587-590.

Kapila A., Addy E.V., Verghese C., Brain A.J., "Intubationg LMA: a preliminary assessment of performance", British Journal of Anaesthesia, 1995; 75:228-229 (Abstract).

Lindholm, "Prolonged Endotracheal Intubation," ACTA Anaesthesiologica Scandinavica 1969 vol. 33 32-46.

Majumder, et al., "Bilateral Lingual Nerve Injury Following the Use of the Laryngeal Mask Airway," Anaesthesia, 1998, vol. 53, pp. 184-186.

Miller, "A pressure regulator for the cuff of a tracheal tube," Anaesthesia, 1992, vol. 47, pp. 594-596.

Muthuswamy, et al., "The Use of Fuzzy Integrals and Bispectral Analysis of the Electroencephalogram to Predict Movement Under Anesthesia," IEEE Transactions on Biomedical Engineering, vol. 46, No. 3, Mar. 1999, pp. 290-299.

Nagai, "Unilateral hypoglossal nerve paralysis following the use of the laryngeal mask airway," Anaesthesia, 1994, vol. 49, pp. 603-604.

Patel, et al., "Trachael tube cuff pressure," Anaesthesia, 1984, vol. 39, pp. 862-864.

Pennant, "Comparison of the Endotracheal Tube and Laryngeal Mask in Airway Management by Paramedical Personnel," Anesth analg 1992:74:531-4.

Pippin, et al., "Long-term tracheal intubation practice in the United Kingdom", Anaesthesia, 1963, vol. 38, pp. 791-795.

Raeder, et al., "Tracheal tube cuff pressures," Anaesthesia, 1985, vol. 40, pp. 444-447.

Seegovin, et al., "Tracheal tube cuff pressure and tracheal mucosal blood flow: endoscopic study of effects of four large volume cuffs," British Medical Journal, vol. 288, Mar. 31, 1984.

Willis, et al., "Tracheal tube cuff pressure," Anaesthesia, 1988, vol. 43, pp. 312-314.

Worthington, et al., "Proceedings of the Anaesthetic Research Society," Br. J. of Anaesthesia 1995 75:228P-229P.

Wynn, et al., "Tongue Cyanosis after Laryngeal Mask Airway Insertion," Anesthesiology, V. 80, No. 6, Jun. 1994, p. 1403.

* cited by examiner

PRIOR ART

INTUBATING LARYNGEAL MASK AIRWAY DEVICE WITH FIBER OPTIC ASSEMBLY

CROSS-REFERENCE TO RELATED APPLICATION

This application is a continuation of and claims priority under 35 U.S.C. §120 to U.S. patent application Ser. No. 10/659,455, filed on Sep. 10, 2003, now U.S. Pat. No. 7,128,071, issued Oct. 31, 2006, entitled INTUBATING LARYNGEAL MASK AIRWAY DEVICE WITH FIBER OPTIC ASSEMBLY.

BACKGROUND OF THE INVENTION

The present invention relates to a laryngeal mask airway device with a fiber optic assembly. More specifically, the present invention relates to an intutbating laryngeal mask airway device with a fiber optic assembly.

The laryngeal mask airway device is a well known device that is useful for establishing airways in unconscious patients. U.S. Pat. No. 4,509,514 is one of the many publications that describe laryngeal mask airway devices. Such devices have been in use for many years and offer an alternative to the older, even better known, endotracheal tube. For at least seventy years, endotracheal tubes comprising a long slender tube with an inflatable balloon disposed at the tube's distal end have been used for establishing airways in unconscious patients. In operation, the endotracheal tube's distal end is inserted through the mouth of the patient, past the patient's laryngeal inlet (or glottic opening), and into the patient's trachea. Once so positioned, the balloon is inflated so as to form a seal with the interior lining of the trachea. After this seal is established, positive pressure may be applied to the tube's proximal end to ventilate the patient's lungs. Also, the seal between the balloon and the inner lining of the trachea protects the lungs from aspiration (e.g., the seal prevents material regurgitated from the stomach from being aspirated into the patient's lungs).

Although they have been enormously successful, endotracheal tubes suffer from several major disadvantages. The principal disadvantage of the endotracheal tube relates to the difficulty of properly inserting the tube. Inserting an endotracheal tube into a patient is a procedure that requires a high degree of skill. Also, even for skilled practitioners, insertion of an endotracheal tube is sometimes difficult or not possible. In many instances, the difficulty of inserting endotracheal tubes has tragically led to the death of a patient because it was not possible to establish an airway in the patient with sufficient rapidity. Also, inserting an endotracheal tube normally requires manipulations of the patient's head and neck and further requires the patient's jaw to be forcibly opened widely. These necessary manipulations make it difficult, or undesirable, to insert an endotracheal tube into a patient who may be suffering from a neck injury.

In contrast to the endotracheal tube, it is relatively easy to insert a laryngeal mask airway device into a patient and thereby establish an airway. Also, the laryngeal mask airway device is a "forgiving" device in that even if it is inserted improperly, it still tends to establish an airway. Accordingly, the laryngeal mask airway device is often thought of as a "life saving" device. Also, the laryngeal mask airway device may be inserted with only relatively minor manipulations of the patient's head, neck, and jaw. Further, the laryngeal mask airway device provides for ventilation of the patient's lungs without requiring contact with the sensitive inner lining of the trachea and the size of the airway established is typically significantly larger than the size of the airway established with an endotracheal tube. Also, the laryngeal mask airway device does not interfere with coughing to the same extent as endotracheal tubes. Largely due to these advantages, the laryngeal mask airway device has enjoyed increasing popularity in recent years.

U.S. Pat. Nos. 5,303,697 and 6,079,409 describe examples of a type of prior art device that may be referred to as an "intubating laryngeal mask airway device." The intubating device is useful for facilitating insertion of an endotracheal tube. After an intubating laryngeal mask airway device has been located in the patient, the device can act as a guide for a subsequently inserted endotracheal tube. Use of the laryngeal mask airway device in this fashion facilitates what is commonly known as "blind insertion" of the endotracheal tube. Only minor movements of the patient's head, neck, and jaw are required to insert the intubating laryngeal mask airway device, and once the device has been located in the patient, the endotracheal tube may be inserted with virtually no additional movements of the patient. This stands in contrast to the relatively large motions of the patient's head, neck, and jaw that would be required if the endotracheal tube were inserted without the assistance of the intubating laryngeal mask airway device.

Figure 1A:
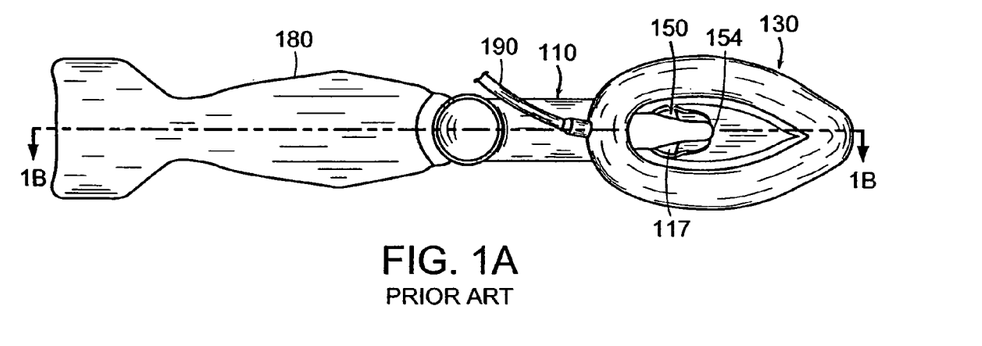
FIG. 1A shows an anterior view of a prior art laryngeal mask airway device.
Figure 1B:
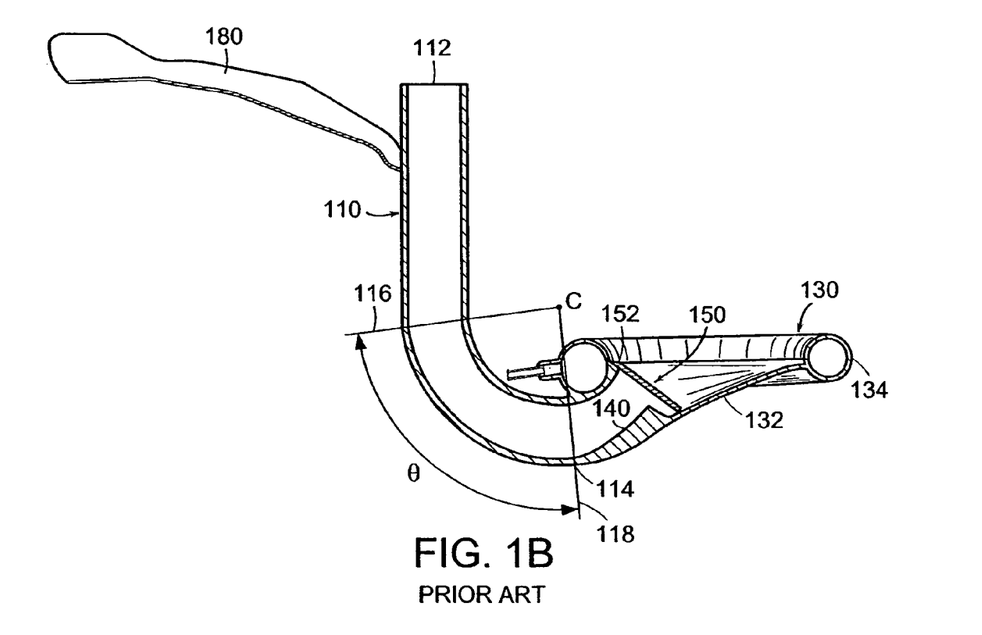
FIG. 1B shows a sectional view taken along the line 1B-1B as shown in FIG. 1A.

One popular form of intubating laryngeal mask airway device has been marketed commercially for many yeas as the "Fastrach" by the Laryngeal Mask Company of Cyprus. FIG. 1A shows a view of the anterior side of a prior art Fastrach device 100. FIG. 1B shows a sectional view of device 100 taken in the direction of the arrows 1B-1B as shown in FIG. 1A.

Device 100 includes a rigid steel airway tube 110, a silicone mask portion 130, a rigid steel handle 180, and an inflation line 190. The handle 180 is attached to airway tube 110 near a proximal end 112 of the tube. Mask portion 130 is attached to airway tube 110 at a distal end 114 of the tube. Mask portion 130 includes a dome shaped backplate 132 and an inflatable cuff 134. Mask portion 130 also includes an epiglottis elevator bar 150. One end 152 of bar 150 is attached to the backplate 132. The other end 154 of the bar 150 is "free floating", or not attached to any other portion of the device. The bar 150 is in effect hinged to the rest of the mask portion. FIGS. 1A and 1B show bar 150 in its resting position (i.e., the position assumed by the bar 150 when no external forces are acting on the bar 150).

Figure 1C:
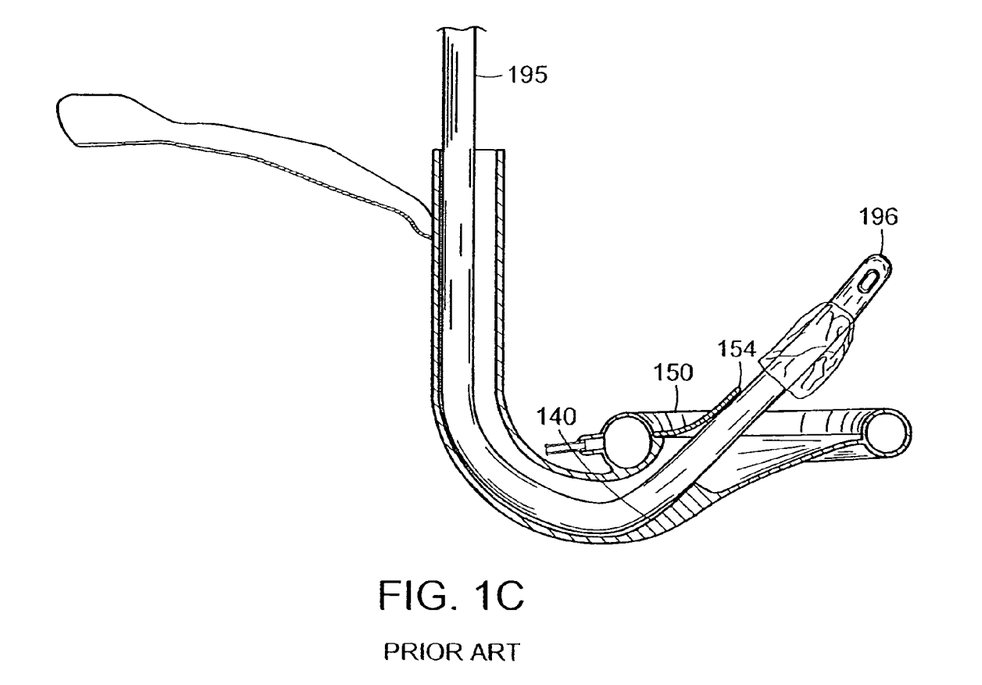
FIG. 1C shows an endotracheal tube being inserted through the device shown in FIG. 1A.

In operation, cuff 134 is deflated, and the mask portion is then inserted through the patient's mouth into the patient's pharynx, while the proximal end 112 of the airway tube and the handle 180 remain outside of the patient's mouth. The handle 180 may be used for manipulating the device. The cuff 134 is then inflated to form a seal around the patient's glottic opening. After the device 100 is so positioned, a distal opening 117 of the device (shown in FIG. 1A) is aligned with the patient's glottic opening and the device provides a sealed airway extending from the proximal end 112 of airway tube 110 to the patient's trachea. When the epiglottis elevator bar 150 is in the resting position shown in FIGS. 1A and 1B, the bar 150 prevents the patient's epiglottis from falling into the bowl shape defined by the inflated cuff and backplate and consequently prevents the epiglottis from blocking the airway passage provided by the device. FIG. 1C shows an endotracheal tube 195 being inserted through device 100. The distal end 196 of the endotracheal tube 195 is inserted into the proximal end 112 of the airway tube and the endotracheal tube 195 is then advanced until the distal end 196 reaches and then passes through the mask portion 130. As shown, as the distal end 196 of the endotracheal tube 195 passes through the mask portion, it moves the distal end (or "free" end) 154 of bar 150 out of the resting position.

As shown in FIG. 1B, the airway tube 110 defines a curved region that extends from a proximal ray 116 to a distal ray 118, the rays 116, 118 meeting at a center of curvature C. As shown in FIGS. 1B and 1C, the backplate 132 defines a ramp 140. The curvature of the airway tube 110 and the ramp 140 make blind insertion of the endotracheal tube possible. That is, when device 100 is inserted in a patient, the curve of the airway tube and the ramp insure that the distal tip of a subsequently inserted endotracheal tube will be aligned with the trachea when it passes through the distal opening of device 100. The angle theta ($\theta$) defined by rays 116, 118 is approximately one hundred twenty degrees. The ramp 140 adds about seventeen additional degrees to this curve such that an endotracheal tube inserted through the device curves through about one hundred thirty seven degrees.

The Fastrach is a reusable device and may be sterilized (and reused) many times before becoming too worn for reuse. Although the Fastrach has performed very well, there remains a need for improved intubating laryngeal mask airway devices.

SUMMARY OF THE INVENTION

These and other objects are provided by an improved intubating laryngeal mask airway device. The device includes an optical system for enabling the physician to insure that the distal end of the device is properly aligned with the patient's trachea before inserting an endotracheal tube through the device. Also, the airway tube may be fabricated from an inexpensive material, such as plastic, instead of steel, so that the device may be used as a disposable device.

Still other objects and advantages of the present invention will become readily apparent to those skilled in the art from the following detailed description wherein several embodiments are shown and described, simply by way of illustration of the best mode of the invention. As will be realized, the invention is capable of other and different embodiments, and its several details are capable of modifications in various respects, all without departing from the invention. Accordingly, the drawings and description are to be regarded as illustrative in nature, and not in a restrictive or limiting sense, with the scope of the application being indicated in the claims.

BRIEF DESCRIPTION OF THE FIGURES

For a fuller understanding of the nature and objects of the present invention, reference should be made to the following detailed description taken in connection with the accompanying drawings in which the same reference numerals are used to indicate the same or similar parts wherein.

DETAILED DESCRIPTION OF THE INVENTION

Figure 2A:
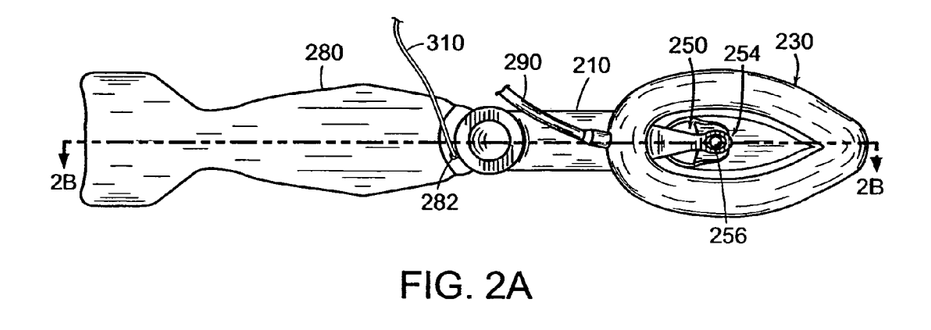
FIG. 2A shows an anterior view of an intubating laryngeal mask airway device constructed according to the invention.
Figure 2B:
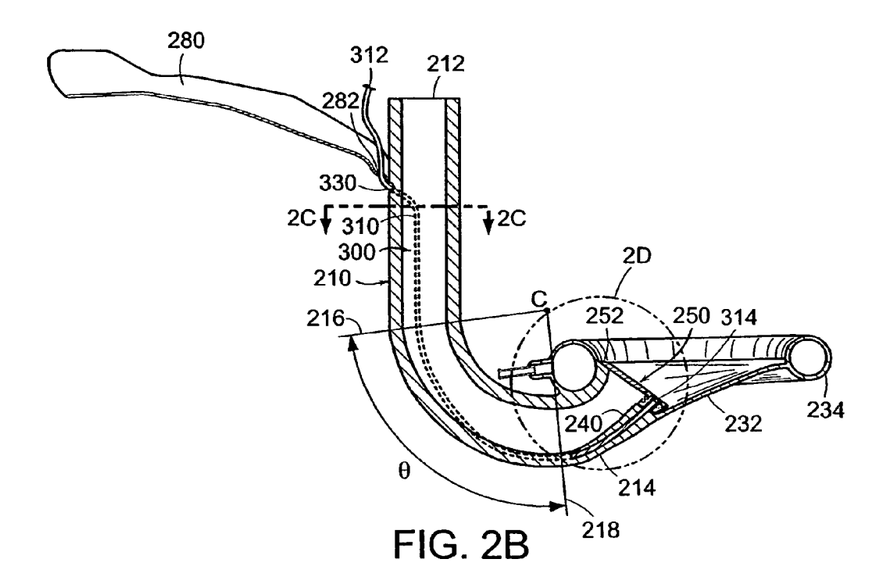
FIG. 2B shows a sectional view taken along the line 2B-2B as shown in FIG. 2A.
Figure 2C:
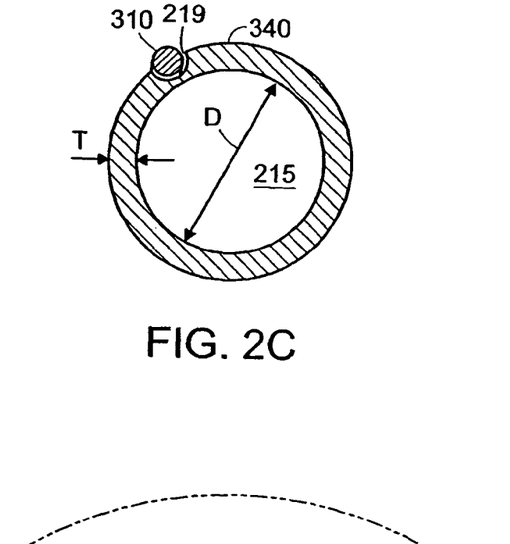
FIG. 2C shows a sectional view taken along the line 2C-2C as shown in FIG. 2B.
Figure 2D:
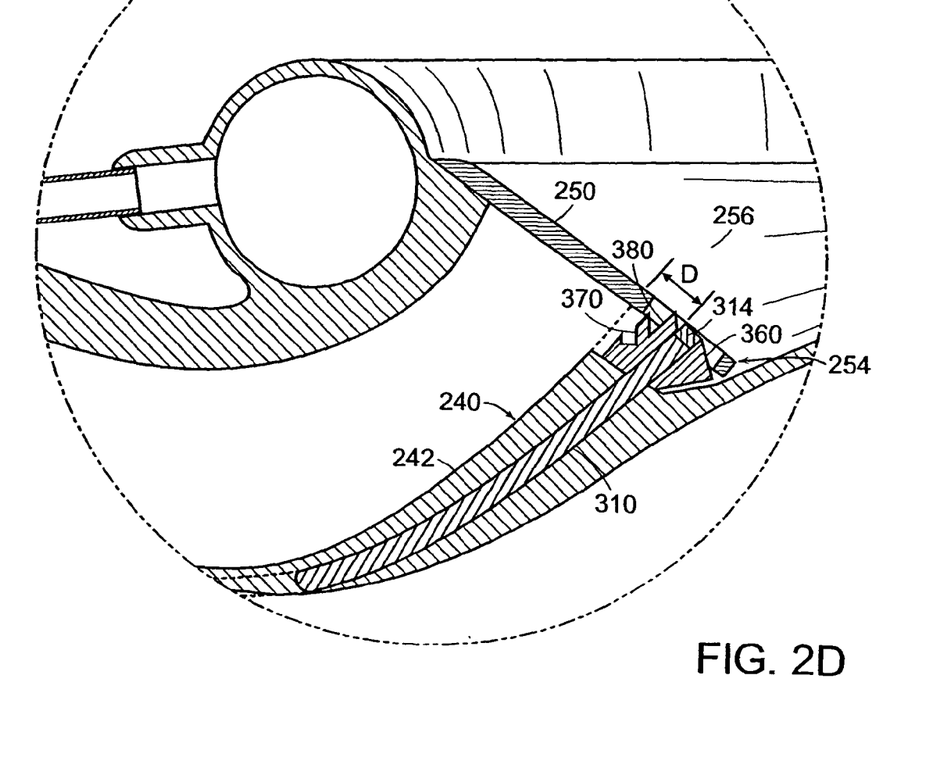
FIG. 2D shows a magnified view of the portion of the device enclosed by the dashed circle labeled 2D as shown in FIG. 2B.

FIG. 2A shows an anterior view of a disposable intubating laryngeal mask airway device 200 constructed according to the invention. FIG. 2B shows a sectional view of device 200 taken in the direction of line 2B-2B as shown in FIG. 2A. FIG. 2C shows a sectional view of device 200 taken in the direction of line 2C-2C as shown in FIG. 2B. FIG. 2D shows a magnified view of the portion of the device 200 enclosed by the dashed circle 2D shown in FIG. 2B.

Device 200 includes a rigid airway tube 210, a silicone mask portion 230, a rigid handle 280, and an inflation line 290. The handle 280 is attached to airway tube 210 near a proximal end 212 of the tube. Mask portion 230 is attached to airway tube 210 at a distal end 214 of the tube. Mask portion 230 includes a dome shaped silicone backplate 232 and an inflatable cuff 234. Mask portion 230 also includes an epiglottis elevator bar 250. One end 252 of bar 250 is attached to the backplate 232. The other end 254 of the bar 250 is "free floating", or not attached to any other portion of the device. As shown in FIG. 2B, the airway tube 210 defines a curved region that extends from a proximal ray 216 to a distal ray 218, the rays 216, 218 meeting at a center of curvature C. As shown in FIGS. 2B and 2C, the backplate 232 defines a ramp 240. As with prior art device 100, the angle theta ($\theta$) defined by rays 216, 218 is about one hundred twenty degrees, and the ramp 240 adds about seventeen degrees to this curve. Different sized mask portions may be attached to the airway tube to adapt the device for larger or smaller patients, and the ramps in the other mask portions can curve by slightly more or less than seventeen degrees.

As shown best in FIG. 2C, airway tube 210 defines a central airway passage 215. Central airway passage 215 extends from the proximal end 212 to the distal end 214 of the tube. When device 200 is inserted in a patient and the cuff 234 is inflated, the cuff 234 forms a seal around the patient's glottic opening and the airway passage 215 communicates with the patient's lungs. When the device 200 is inserted in a patient, the handle 280 and the proximal end 212 of the airway tube remain outside of the patient's mouth, and the device provides a sealed airway passage that extends from the proximal end 212 of the airway tube, through passage 215, to the patient's glottic opening.

Comparing FIGS. 1A-1B and 2A-2B, it will be appreciated that device 200 has many features in common with device 100. Both devices include silicone mask portions, rigid airway tubes, and rigid handles. However, whereas reusable device 100 includes a steel airway tube and a steel handle, device 200 is disposable and includes a plastic (e.g., polycarbonate) airway tube 210 and a plastic (e.g. polycarbonate) handle 280. The airway tube 210 and handle 280 of device 200 are preferably made from a rigid material such as polycarbonate. Since it is made from rigid plastic instead of steel, the wall of airway tube 210 is thicker than the wall of airway tube 110. The thickness T of the wall of airway tube 210, as shown in FIG. 2C, is substantially equal to 1.9 millimeters. The diameter D of the airway passage 215 defined by tube 210, as shown in FIG. 2C, is substantially equal to 12.2 millimeters.

Another important difference between devices 100 and 200 is that device 200 includes a fiber optic system 300. Fiber optic system 300 includes a bundle of optical fibers 310 that extend from a proximal end 312 to a distal end, and a lens 314 is mounted to the optical fibers at their distal end. When the device 200 is inserted in a patient, the proximal end 312 of bundle 310 remains outside of the patient's mouth and may be connected to standard viewing devices (e.g., screens or eyepieces). The lens 314 is disposed near ramp 240.

Although the curve of the airway tube and the shape of the ramp generally facilitate blind insertion of an endotracheal tube, the fiber optic system 300 advantageously provides a view of the patient's anatomy that is aligned with the distal end of device 200. This enables alignment between the distal end of the device and the patient's glottic opening to be adjusted before attempting to insert an endotracheal tube through the device 200. If the distal end of the device is not perfectly aligned with the patient's glottic opening, as shown by the fiberoptic view obtained, the handle 280 may be used to make minor adjustments in the position of device 200 to thereby facilitate subsequent insertion of an endotracheal tube. This stands in contrast with prior art devices in which the glottic opening is sought and identified by means of an expensive mechanism built into the fiberoptic cable itself which allows its distal tip to be flexed in a single plane.

As shown best in FIG. 2C, in addition to the central airway passage 215, the airway tube 210 also defines a notch 219. Notch 219 is defined in the wall of tube 210 and is outside of, and does not communicate with, the airway passage 215. Notch 219 houses a portion of the bundle 310 of optical fibers. As shown in FIG. 2B, notch 219 extends from a location 330 on the airway tube to the ramp 240. Location 330 is near the junction of handle 280 and tube 210 and is between that junction and the distal end of the tube. As noted above, the bundle 310 of optical fibers extends from proximal end 312 to lens 314. A free section of the bundle 310 extends from proximal end 312, through a hole 282 defined in handle 280, to the point 330. A "housed" or "protected" section of the bundle 310 extends from point 330 to the lens 314.

As shown best in FIGS. 2A and 2D, the epiglottis elevator bar 250 is "paddle shaped" and the distal end 254 defines an aperture 256. When bar 250 is in its resting position (i.e., when cuff 234 is inflated and no external forces are acting on bar 250), the lens 314 of fiber optic system 300 is aligned with aperture 256 so that the bar 250 does not occlude the view provided by the lens.

In FIG. 2C, the apex of the airway tube 210 is indicated at 340. Apex 340 is the point of the tube that will be contacted by the patient's upper teeth when the device is inserted in a patient. As shown in FIG. 2C, the notch 219 is offset from the apex 340 in the region of the airway tube near location 330 to insure that the patient's teeth do not contact and damage the bundle 310 of optical fibers. Although the notch 218 is offset from the apex near point 330, as the notch 219 progresses down the tube towards the mask portion, the notch 219 assumes a more central location such that at the distal end, the lens 314 is centrally aligned with the aperture 256 in the epiglottis elevator bar 250 as shown in FIGS. 2A and 2D.

Bundle 310 of optical fibers generally contains two sets of fibers. One set carries light from the proximal end 312 to the lens so as to illuminate the patient's anatomy. The other set carries light received by lens 314 back to the proximal end so as to provide a view of the patient's anatomy. In the illustrated embodiment, both sets of fibers extend through a single notch 219. However, it will be appreciated that the airway tube may define two notches and each set of fibers may be housed in its own notch. In such embodiments, the notches can meet at the ramp 240 so that both sets of fibers and the lens are housed in a single aperture extending through the ramp 240.

As shown best in FIG. 2D, device 300 also includes a collar 360. The collar 360 is disposed against the distal end of ramp 240 and houses the distal most portion of the bundle 310 and the lens 314. Collar 360 may be fabricated as an integral part of the backplate portion 230. Mask portion 230, which includes the dome shaped backplate 232, ramp 240, collar 360, and cuff 234 may be formed, for example, by injection molding, as a single monolithic part.

Figure 3:
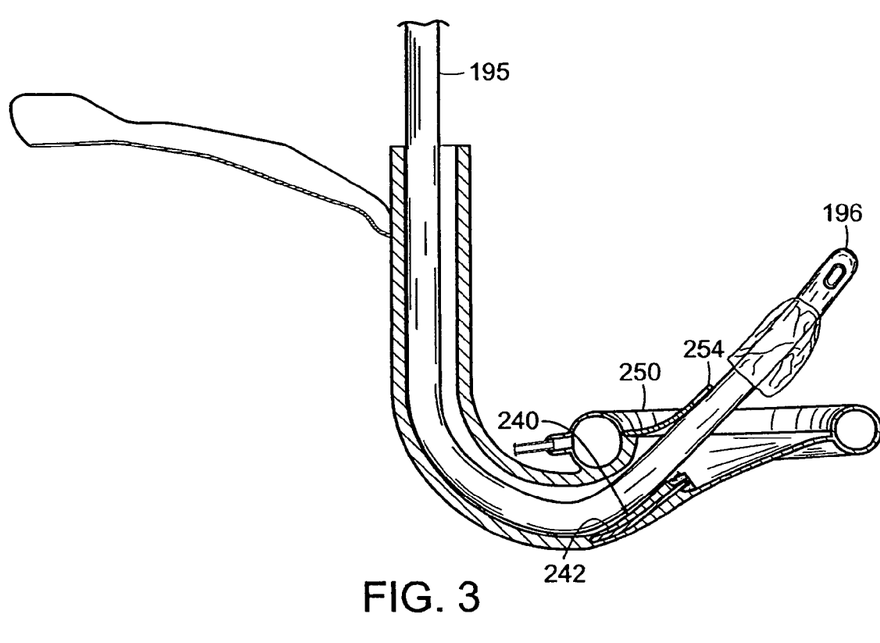
FIG. 3 shows an endotracheal tube being inserted through an intubating laryngeal mask airway device constructed according to the invention.

FIG. 3 shows an endotracheal tube 195 being inserted through device 200. One useful function performed by collar 360 is that it insures that the endotracheal tube 195 always remains spaced apart from the lens 314. The lens 314 typically defines a sharp right angle surface and it is therefore desirable to space the lens 314 away from the endotracheal tube 195 to insure that the lens 314 does not contact, and possibly tear, the cuff of the endotracheal tube 195. Referring back to FIG. 2D, collar 360 insures that the lens 314 is spaced apart from a line extending from supporting surface 242 by a distance D. The distance D may be equal to about two millimeters.

In addition to defining a central aperture for housing the distal end of bundle 310 and lens 314, the collar 360 also defines a first notch 370 and a second notch 380. Notches 370 and 380 help protect the lens 314. Lubricant is often applied to the cuff of an endotracheal tube 195 before the tube is inserted through an intubating device as shown in FIG. 3. It is desirable to prevent this lubricant from falling onto, and obstructing the view provided by, the lens 314. As an endotracheal tube 195 is inserted through device 200, the notch 370 collects any lubricant that might be scraped off of the tube 195 and thereby prevents that lubricant from falling onto the lens 314. Similarly, as an endotracheal tube 195 is withdrawn through device 200, the notch 380 collects any lubricant that might be scraped off of the tube 195 and again thereby prevents that lubricant from falling onto the lens 314. Since it may sometimes be necessary to withdraw one endotracheal tube and then insert another, it is desirable to protect the lens 314 from lubricant that may be scraped off of an endotracheal tube as the tube is withdrawn.

The upright edge of notch 380 can be spaced apart from the distal end of collar 360 by about 2.5 millimeters. The upright edge that defines the proximal end of notch 370 may be spaced apart from the distal end of collar 360 by about five millimeters. Notches 370 and 380 may be about 1.5 millimeters deep.

Since certain changes may be made in the above apparatus without departing from the scope of the invention herein involved, it is intended that all matter contained in the above description or shown in the accompanying drawing shall be interpreted in an illustrative and not a limiting sense.

What is claimed is:

1. A laryngeal mask airway device, comprising:
   A. a rigid airway tube extending from a proximal end to a distal end, the airway tube defining an internal passage;
   B. a mask portion coupled to the distal end of the airway tube, the mask portion including a dome shaped backplate and an inflatable cuff, the cuff defining a central opening at least when inflated, the mask portion being insertable through a mouth of a patient to an inserted location within the patient, the cuff surrounding a glottic opening of the patient when inflated and when the mask portion is at the inserted location, a sealed airway passage extending from the proximal end of the tube through the internal passage to the glottic opening when the cuff is inflated and when the mask portion is at the inserted location, the mask portion including an epiglottis elevator bar, the bar extending from a proximal end to a distal end, the distal end of the bar defining an aperture, the bar being positionable in a resting position and an open position, the backplate defining a ramp, the ramp defining a notch; and C. a viewing system having a distal end and a proximal end, the distal end of the viewing system being positioned such that light rays may pass from a portion of the patient's anatomy through the aperture defined by the epiglottis elevator bar to the distal end of the viewing system when the bar is in the resting position and the mask portion is at the inserted location, the proximal end of the viewing system being disposed outside the patient's mouth when the mask portion is at the inserted location, the distal and the proximal ends of the viewing system being in communication such that the proximal end of the viewing system provides a view of the portion of the patient's anatomy.

2. The device of claim 1, wherein the viewing system includes one or more optical fibers.

3. The device of claim 2, wherein at least one optical fiber includes a lens connected to a distal end of the at least one fiber.

4. The device of claim 1, further comprising a collar defining a portion of the ramp, the collar defining the notch and an aperture, the light rays passing through the aperture when the mask portion is at the inserted location.

5. The device of claim 1, the airway tube further defining a groove, the groove extending along a length of the tube from a location on the tube towards the distal end of the tube, a part of the viewing system extending through the groove.

6. The device of claim 5, the part of the viewing system extending through the groove including one or more optical fibers, each of the one or more optical fibers having a proximal end and a distal end.

7. The device of claim 6 further including a lens connected to the distal end of at least one of the one or more optical fibers.

8. The device of claim 1, further comprising a viewing device connected to the proximal end of the viewing system.

* * * * *